United States Patent [19]

Molinski et al.

[11] 4,042,676

[45] Aug. 16, 1977

[54] TECHNETIUM-99m LABELED RADIODIAGNOSTIC AGENTS FOR LIVER AND BONE MARROW SCANNING AND METHOD OF PREPARATION

[75] Inventors: Victor Joseph Molinski, Ridgewood, N.J.; Frank Raymond Peacock, Newburgh, N.Y.

[73] Assignee: Union Carbide Corporation, New York, N.Y.

[21] Appl. No.: 621,087

[22] Filed: Oct. 9, 1975

[51] Int. Cl.² .................. A61K 29/00; A61K 43/00
[52] U.S. Cl. .......................... 424/1; 252/301.1 R
[58] Field of Search ................. 424/1; 252/301.1 R

[56] References Cited

U.S. PATENT DOCUMENTS 3,875,299  4/1975  Winchell et al. .................. 424/1

OTHER PUBLICATIONS

Aburano et al., Life Sciences, vol. 12, June 30, 1975, Abstract No. 33622, p. 3371.
Columbetti, Radiobiol.-Radiother, Jan. 1974, pp. 47–51.
Johnson et al., Journ. of Nuclear Medicine, vol. 11, No. 1, (1970) pp. 564–565.
Sewakar et al., Nuclear Medicine, vol. XIV, No. 1, Mar. 31, 1975, pp. 46–51.
Subrumanian et al., J. of Nucl. Med., vol. 11, No. 6, 1970, pp. 365–366.

*Primary Examiner*—Benjamin R. Padgett
*Assistant Examiner*—Christine M. Nucker
*Attorney, Agent, or Firm*—Israel Blum

[57] ABSTRACT

An improved technetium-99m labeled colloid and method of preparation comprising reducing technetium-99m with stannous oxalate and stabilizing with sodium phytate. This radiodiagnostic agent is useful in the scintigraphic examination of the recticuloendothelial system, particularly the liver. In addition, by autoclaving this product with saline, it becomes a superior bone marrow scanning agent.

24 Claims, No Drawings

TECHNETIUM-99M LABELED RADIODIAGNOSTIC AGENTS FOR LIVER AND BONE MARROW SCANNING AND METHOD OF PREPARATION

FIELD OF THE INVENTION

This invention relates to improved technetium-99m labeled radiodiagnostic agents useful in liver and bone marrow scanning applications and methods for their preparation. In particular, this invention relates to technetium labeled radiodiagnostic agents containing sodium phytate and stannous ion chelated with oxalate and methods for their preparation. In another aspect, this invention relates to non-radioactive radiodiagnostics containing sodium phytate and stannous ion chelated with oxalate, the radiodiagnostics being suitable for liver scanning and bone marrow scanning when labeled with $^{99m}$Tc and a method for their preparation.

DESCRIPTION OF THE PRIOR ART

Technetium-99m has become an extremely useful tool in medical applications, particularly as a radionuclide tracer in both medical research and diagnosis. Technetium99m's short half-life (6 hours) reduces exposure of the organs to radiation; its gamma radiation energy (140 Kev.) not only provides sufficient tissue penetration but also is readily collimated; and absence of beta radiation permits millicurie amounts of the radionuclide to be administered orally or by injection into the patent without harmful radiation dosage. Due to these physical characteristics, technetium-99m is frequently used as radiocolloid or in a complex or in combination with appropriate carriers for in vivo diagnostic tests such as scintigraphic examinations of the liver, lung, blood pool, bone and tumors. Because no operation is required for diagnosis, the popularity of this method has increased in recent years.

Chemically, technetium belongs to group VII-A of the Periodic Table of the Elements and there are many similarities between its chemistry and the chemistry of manganese and rhenium. In aqueous solution, the most stable form of technetium is the pertechnetate ion (TcO$_4$), which is similar to iodide in its biological distribution, thereby rendering it useful in scanning. Moreover, the ability of technetium to combine with other materials when reduced to lower oxidation states makes it useful both when chelated with an appropriate carrier for kidney or blood function studies and also when trapped physically as a colloid for liver studies or as a particle for lung studies. Technetium is generally used in the form of sodium pertechnetate in an isotonic saline solution for labeling diagnostic agents.

Technetium-99m labeled Complexes containing a number of components including stannous chloride and gluconate, mercaptan and thioketal, sodium citrate have been used for renal scintigraphy. In addition, such radiocolloids as $^{99m}$Tc-sulfur colloids prepared from sodium thiosulfate or hydrogen sulfide, $^{99m}$Tc-technetium dioxide colloids, $^{99m}$Tc-stannous chloride colloids and $^{99m}$Tc-phytate colloids prepared from sodium phytate and stannous chloride have been used for liver scanning. Stannous oxide colloids prepared from stannous chloride, buffered with sodium phosphate, have been used for bone marrow imaging.

SUMMARY OF THE INVENTION

It is an object of this invention to provide technetium-99m labeled radiodiagnostic agents which can be used as dual purpose imaging agents for the liver and bone marrow and a method for their preparation. Another object of this invention is to provide a stable colloid containing stannous oxalate and sodium phytate and a method for its preparation. Still another object of the invention is to provide a packaged stannous oxalate-sodium phytate reagent for preparing size stabilized technetium-99m labeled colloids and a simple method for using the reagent with generally available technetium pertechnetate saline solutions. Other objects and advantages of the invention will become apparent to those skilled in the art upon consideration of the following description of the preferred embodiments of the colloids, the packaged reagent and the methods for their preparation and other teachings herein set forth.

This invention is based upon the discovery that stannous oxalate and sodium phytate, when mixed in the proper proportions, produce a stable radiocolloid which can be lyophilized. Although the nature of this mechanism is not fully understood, it is believed that the radiocolloid is formed in vitro, not in vivo. When the lyophilized product is reconstituted with saline solutions of technetium-99m, a radiocolloid of a particle size less than about 5 microns is formed. This radiocolloid, when injected intravenously into a patient, is trapped in phagocytic Kupffer cells of the liver. This same lyophilized product can be reconstituted with small amounts of saline or aqueous solution and autoclaved. The autoclaved colloid has a reduced particle size of less than about 1 micron, can be tagged with technetium-99m and used for bone marrow imaging by trapping the smaller particle in the recticuloendothelial cells of the bone marrow.

It has been discovered that stannous oxalate provides a superior colloids which is more stable to air oxidation and autoclaving than tin-phytate colloids which have utilized stannous chloride. Generally, stannous compounds are easily oxidized to stannic compounds in aqueous solution. Moreover, in the absence of strongly complexing anions, tin having a +2 oxidation state is extensively hydrolyzed in aqueous solution. The hydrolyzed and oxidized compounds of tin formed in aqueous solution produce insoluble compounds. These insoluble compounds prevent the reaction of tin in the preparation of a radiodiagnostic agent. This problem has been overcome by the use of stannous ion chelated with oxalate. By chelating with tin, oxalate substantially prevents deleterious oxidation of tin and the formation of stannic ions in solution. Otherwise, oxidants such as peroxides, hydroxide radicals and the like, formed as a result of radiolysis, would consume ionized tin. According to this invention, however, this is prevented by employing stannous oxalate which is not strongly ionized in aqueous solution whereas stannous chloride is.

According to this invention, a radiodiagnostic agent suitable for liver scanning when labeled with 99mTc may be prepared by the method comprising the steps of dissolving a first predetermined amount of sodium phytate in an aqueous solution substantially free from entrained oxygen; dissolving a second predetermined amount of stannous oxalate in a non-oxidizing acid, the first predetermined amount being at least equivalent by weight to the second predetermined amount; contacting the dissolved solution of sodium phytate with the dissolved solution of stannous oxalate to form an oxalate-phytate containing solution; and adjusting the pH of the oxalate-phytate solution to between about 4 and about 7, preferably about 6. The second predetermined amount should be present in an amount at least sufficient to chemically reduce the total amount of technetium present.

It may be desirable to adjust the concentration of the solution to a predetermined concentration of sodium phytate-stannous oxalate per ml of the solution. It also may be desirable to lyophilize the solution to a solid at a temperature below about 30° C, preferably between about 30° C and about −10° C when it is desirable to store the solution for months before use, or the solution may be used in liquid form for a shorter time period. When a solution suitable for liver scanning is desired the lyophilized residue may be redissolved in an aqueous solution.

It is desirable to removed an entrained or dissolved oxygen from the solution in an amount sufficient to prevent oxidation of the stannous to stannic. As previously described, such oxidation would prevent complete reduction of the technetium. Therefore, an aqueous solution may be purged with non-oxidizing gas to replace and remove the entrained oxygen gas. The non-oxidizing gas should not be appreciably absorbed by the aqueous solution nor be toxic. Suitable non-oxidizing gases include nitrogen, carbon dioxide, noble gases or the like.

Suitable nonoxidizing acids inlcude hydrochloric, acetic, sulfuric and phosphoric and the like.

According to this invention, sodium phytate is present in an amount at least substantially equivalent by weight to stannous oxalate. Preferably, the ratio by weight of sodium phytate to stannous oxalate is at least about 3 to 1, more preferably at least 13 to 1 and most preferable between about 3 to 1 and about 20 to 1. At ratios by weight of sodium phytate to stannous oxalate of less than about 1 to 1, the stability of the radiocolloid produced according to the method of this invention is reduced causing unsatisfactory variances in particle size and unbound technetium which is undesirable.

In another aspect, this invention relates to a colloid which is suitable for bone marrow scanning when labeled with $^{99m}$Tc which colloid is prepared by autoclaving the solution or reconstituted lyophilized product of stannous oxalate-sodium phytate at a predetermined temperature for a predetermined time to form the colloid having a particle size less than about 1 micron and a pH between about 3 and about 7.

In a preferred embodiment of the method of this invention, sodium phytate is dissolved in nitrogen purged water. The stannous oxalate is dissolved in a non-oxidized acid, preferably concentrated hydrochloric acid, and added to the sodium phytate solution. The pH is adjusted to between about 4 and about 7, but preferably about 6, with a strong base, preferably 1 normal sodium hydroxide. The solution is adjusted to a predetermined volume with nitrogenpurged water and filtered. The solution is then dispensed in 1 cc aliquots into serum vials and can be used in liquid form, but is preferably lyophilized at a temperature below about 30° C, preferably between about 30° c and about −10° C.

In another embodiment of this invention, a solution or reconstituted lyophilized product of stannous oxalate-sodium phytate may be autoclaved and up to about 5 ml of technetium-99m in saline is added thereto. This tagged colloid can be used for imaging the bone marrow. According to the method of this invention, in this embodiment, the solution of stannous oxalate-sodium phytate or the reconstituted lyophilized stannous oxalate-sodium phytate (which has been reconstituted with about 0.5 to about 1 ml of saline) is autoclaved at a temperature of from about 240° F to about 290° F, but preferably at about 270° F for from about 1 hour to about 6 hours, but preferably about 2 hours, and pressures from about 10 to about 43 psi, preferably about 28 psi.

To prepare the radiodiagnostic bone marrow agent, up to about 5 ml of technetium-99m in the form of sodium pertechnetate in saline may be added to the autoclaved colloid. The volume of solution injected into the patent depends on activity concentration, which typically is about 1 to about 4mCi $^{99m}$Tc.

The following examples illustrate the invention:

EXAMPLE I

A stannous oxalate colloid was prepared in the following manner: 200 mg. stannous oxalate ($SnC_2O_4$) was dissolved in 100 ml of water which had been purged with nitrogen. 10 ml of the solution formed by dissolving the stannous oxalate in water purged with nitrogen was diluted to 100 ml with water which had also been purged with nitrogen. In this manner, the pH of the diluted solution was adjusted to 4.1. The so diluted solution was filtered through a 0.22 $\mu$ filter and 1 ml of the filtered solution was dispensed into a 10 cc serum vial. Similarly, samples of the filtered solution were also freeze dried.

The liquid and lyophilized samples were tagged with 3 cc of low concentration $^{99m}$Tc and a bioassay in mice and chromatographic analyses were performed. The % binding efficiency of the chemical labeling procedure and stability of the preparation were determined by ascending paper chromatography using Whatman No. 1 paper strips in 85% methanol and scanning on a radiochromatographic scanner. The bioassay in mice was determined by injecting 0.2 ml into the tail veins of mice and sacrificing them after 1/2 hour uptake times. The results are summarized in Table I below:

TABLE I

| Tissue Distribution of $^{99m}$Tc-Stannous Oxalate Before and After Lyophilization | | |
|---|---|---|
| | Bioassay in Mice % of Injected Activity | |
| Organ | Liquid | Lyophilized* |
| Liver | 91.7 | 93.4 |
| Spleen | 1.7 | 2.6 |
| Lungs | 0.6 | 2.6 |
| Intestines | 1.6 | 0.2 |
| Kidneys | 0.7 | 0.2 |
| Heart | 0.0 | 0.0 |
| Carcass | 3.8 | 1.0 |

*Chromatographic Analysis > 99% bound, uptake time 30 minutes.

As the results summarized in Table I indicate, after freeze drying, a stannous oxalate colloid by itself would be unsatisfactory as a liver scanning agent because there is an agglomeration of particles which causes an increased lung uptake.

EXAMPLE II

Sodium phytate was added to stabilize a stannous oxalate colloid according to the following procedure: 90 ml. of water were purged with nitrogen for 1 hour. The pH of the purged water was adjusted to 3.0 using 0.1N HCl. 400 mg of sodium phytate was dissolved in the nitrogenpurged water raising the pH to about 10. The pH of the solution was readjusted to 3.0 using 1N HCl. 20 mg of stannous oxalate was added and stirred into the solution until dissolved therein. 1 ml of the solution was then dispensed through a 0.22 μ filter into a 10 cc serum vial and subsequently freeze-dried.

The sodium phytate-stannous oxalate preparation described above was tested by performing a bioassay in mice. The lung uptake was very low and the liver uptake was satisfactory. When compared with the results of Example I where no phytate was employed, it can be appreciated that the addition of sodium phytate stabilized the particle size of the oxalate colloid and prevented high lung uptake. The preparation described above was tagged with 3cc of low concentration $^{99m}$Tc and injected into 4 mice. The results of a bioassay on mice are summarized in Table II below:

TABLE II

Tissue Distribution of Stannous Oxalate-Sodium Phytate

| Organ | Bioassay in Mice* % of Injected Activity |
|---|---|
| Liver | 91.3 |
| Spleen | 2.5 |
| Lungs | 0.1 |
| Intestines | 1.1 |
| Kidneys | 0.6 |
| Heart | 0.1 |
| Carcass | 4.3 |

*Average of 4 mice, uptake time ½ hour.

EXAMPLE III

Using the same procedure as described in Example II, three batches of technetium-99m labeled stannous oxalate-sodium phytate colloid were prepared. In the preparation of these three batches, however, the sodium phytate concentration was held constant at 400 mg per 100 ml while the concentration of stannous oxalate employed was varied from 10 to 40 mg per 100 ml. The three concentrations tested were 10, 20 and 40 mg stannous oxalate per 100 ml. All three concentrations gave similar bioassay results in mice after 30 minutes uptake time. However, chromatographic results showed that the 10 mg stannous oxalate per 100 ml concentration only gave 76% bound $^{99m}$Tc which is unsatisfactory while the 40 mg stannous oxalate per 100 ml gave 91% bound $^{99m}$Tc which is preferable. Therefore, at least 10 mg of stannous oxalate is necessary to chemically reduce the total technetium present.

EXAMPLE IV

Using the same procedure as described in Example II, three batches of $^{99m}$Tc labeled stannous oxalate-sodium phytate were prepared. In the preparation of these three batches, however, the stannous oxalate concentration was kept constant at 20 mg per 100 ml while the concentration of sodium phytate (inositol hexaphosphate) was varied from 100 to 600 mg/100 ml. Concentrations of 100, 400 and 600 mg sodium phytate per 100 ml were used. Autoradiographs on mice showed excellent liver uptake and the results of a bioassay on mice after 30 minutes uptake time are summarized in Table III below:

TABLE III

Variation in Concentration of Phytate in Stannous Oxalate Colloid

| Organ | Bioassay in Mice % of Injected Activity | | |
|---|---|---|---|
|  | 100 mg. sod. phytate | 400 mg. sod. phytate | 600 mg. sod. phytate |
| Liver | 84.1 | 91.8 | 92.2 |
| Spleen | 2.6 | 2.4 | 1.7 |
| Lungs | 0.3 | 0.1 | 0.2 |
| Intestines | 1.8 | 0.9 | 1.2 |
| Kidneys | 0.9 | 0.4 | 0.5 |
| Heart | <0.1 | 0.1 | <0.1 |
| Carcass | 10.3 | 4.3 | 4.2 |

EXAMPLE V

Using the same procedure as described in Example II, six batches of $^{99m}$Tc-labeled stannous oxalate-sodium phytate colloid were prepared. In the preparation of these batches, however, 1N HCl was used to adjust the pH of the final products to 3.0, 4.0, 5.0, 6.0, 7.0 and 8.0, respectively, before lyophilization. Then the batches were each aliquoted into vials and lyophilized. Autoradiographs on mice showed excellent liver uptake and comparable results at these varying pHs. The results of a bioassay in mice, after 30 minutes uptake time are summarized in Table IV below:

TABLE IV

Effect of pH on Stannous Oxalate Colloid

| Organ | Bioassay in Mice % of Injected Activity | | | | | |
|---|---|---|---|---|---|---|
|  | pH 3.0 | pH 4.0 | pH 5.0 | pH 6.0 | pH 7.0 | pH 8.0 |
| Liver | 91.9 | 89.8 | 92.4 | 91.9 | 90.4 | 88.0 |
| Spleen | 2.4 | 2.6 | 2.0 | 2.8 | 2.0 | 1.7 |
| Lungs | 0.1 | 0.2 | 0.2 | 0.1 | 0.2 | 0.2 |
| Intestines | 1.0 | 1.4 | 1.1 | 1.2 | 2.2 | 3.0 |
| Kidneys | 0.6 | 0.6 | 0.5 | 0.4 | 1.0 | 1.2 |
| Heart | <0.1 | <0.1 | 0.1 | <0.1 | <0.1 | <0.1 |
| Carcass | 4.0 | 5.4 | 3.8 | 3.6 | 4.2 | 5.7 |

EXAMPLE VI

Using the following procedure, a 200 ml batch of sodium phytate-stannous oxalate colloid was prepared. 200 ml. of water was purged with nitrogen for 45 minutes in a 250 ml three-neck flask. 800 mg of sodium phytate was weighed and added to the flask with stirring resulting in a pH of about 10. The solution was stirred for 10 minutes or until the phytate had dissolved. The pH was adjusted to 6.0 with 1N HCl (about 2.7 ml). 80 mg of stannous oxalate were weighed and added to the flask while the solution was being constantly stirred. After approximately 20 minutes, the pH was adjusted to 6.0 with 1N NaOH. The entire solution was filtered through a 0.22 μ MILLIPORE membrane filter. 1 cc aliquots of the final reagent were dispensed into 10 cc serum vials which were placed in a freeze dryer and lyophilized at 0° C and 400 microns of Hg. vacuum for 16 – 24 hours. The lyophilized product comprised 4 mg sodium phytate, 0.4 mg stannous oxalate and sodium chloride formed from pH adjustment.

The final reagent was incubated for 30 minutes. A technetium-99m radiodiagnostic agent suitable for liver scanning was prepared by the addition of 3 ml of low concentration $^{99m}$Tc (30 mCi of $^{99m}$Tc) to the final reagent. 0.2 cc was injected into 20 mice and after various time intervals, the mice were sacrificed and a bioassay performed. The results of Table V below indicate that the radiodiagnostic agent is still in the lever after six hours, which is comparable to other commercial radiocolloid preparations. The results of the biossay in mice are summarized in Table V below:

TABLE V

Organ Distribution of Sodium Phytate-Stannous Oxalate Colloid in Mice
Bioassay in Mice % of Injected Activity

| Uptake Time | Liver | Spleen | Lung | Kidney | Heart | Stomach | Intestines | Carcass |
|---|---|---|---|---|---|---|---|---|
| 10 min. | 91.5 | 2.9 | 0.1 | 0.6 | <0.1 | 0.2 | 0.9 | 3.7 |
| 20 min. | 90.3 | 2.2 | 0.1 | 0.9 | <0.1 | 0.2 | 0.7 | 5.7 |
| 30 min. | 92.4 | 2.0 | 0.2 | 0.3 | <0.1 | 0.2 | 1.3 | 3.5 |
| 1 hr. | 91.7 | 2.2 | 0.2 | 0.7 | <0.1 | 0.2 | 0.8 | 4.1 |
| 2 hr. | 92.2 | 2.5 | 0.1 | 0.6 | <0.1 | 0.4 | 1.2 | 2.9 |
| 3 hr. | 90.5 | 3.6 | 0.1 | 0.5 | <0.1 | 0.2 | 1.8 | 3.2 |
| 4 hr. | 91.0 | 3.2 | <0.1 | 0.8 | <0.1 | 0.1 | 1.3 | 3.5 |
| 5 hr. | 92.0 | 2.4 | <0.1 | 0.8 | <0.1 | 0.1 | 2.2 | 3.5 |
| 6 hr. | 87.9 | 3.4 | 0.1 | 1.0 | <0.1 | 0.2 | 2.1 | 5.2 |

A six hour blood clearance study was performed on mice using the sodium phytate-stannous oxalate reconstituted with 3 cc of low concentration $^{99m}$Tc. The material was tested chromatographically in 85% methanol and showed > 99% binding. The blood was collected in capillaries, weighed, counted and compared to a standard $^{99m}$Tc solution.

In addition, a six hour blood clearance study was performed on a rabbit using the stannous oxalate-sodium phytate reconstituted with 3 cc of low concentration $^{99m}$Tc. The rabbit was injected with 0.4 cc of the $^{99m}$Tc-tagged colloid. Blood samples were collected at various time intervals and compared to a standard $^{99m}$Tc solution. The rabbit was sacrificed and the liver and spleen removed, weighed, and activity per gram of tissue was determined. The spleen to liver ratio was 1.1 to 1 which is a favorable ratio for liver-spleen imaging. The results of the blood clearance in mice and a rabbit are summarized in Table VI below:

TABLE VI

Blood Clearance of Sodium Phytate-Stannous Oxalate*
in Mice and a Rabbit

| Mice | | Rabbit | |
|---|---|---|---|
| Uptake Time | % of Injected Activity in Blood | Uptake Time | % of Injected Activity in Blood |
| 10 min. | 2.1 | 10 min. | 2.9 |
| 20 min. | 0.7 | | |
| 30 min. | 0.9 | 30 min. | 2.9 |
| 1 hr. | 0.4 | 1 hr. | 2.2 |
| 2 hr. | 0.5 | 2 hr. | 1.5 |
| 3 hr. | 0.3 | 3 hr. | 1.9 |
| 4 hr. | 0.4 | 4 hr. | 3.2 |
| 6 hr. | 0.3 | 6 hr. | 1.4 |

*Reconstituted at pH 6.0

In another test, the stannous oxalate-sodium phytate prepared and tagged with $^{99m}$Tc as described hereinabove was injected into 6 mice. The mice were placed in a metabolism cage and collective urine samples were periodcally counted and urine clearance of $^{99m}$Tc activity was compared to injected activity. The results are summarized in Table VII below:

TABLE VII

Urine Clearance of Sodium Phytate-Stannous
Oxalate in Mice*

| Time after Injection | % Activity per Sample | % of Injected Activity Excreted |
|---|---|---|
| 30 min. | 0.3 | 0.3 |
| 1 hr. | 2.8 | 3.1 |
| 2 hr. | 2.0 | 5.1 |
| 3 hr. | 2.4 | 7.5 |
| 4 hr. | 0.9 | 8.4 |
| 5 hr. | 1.8 | 10.2 |
| 6 hr. | 1.0 | 11.2 |

*Reconstituted at pH 6.0

A vial of stannous oxalate-sodium phytate was reconstituted with 3.0 cc of low concentration $^{99m}$Tc. The tagged compound was analyzed chromatographically. After 30 minutes, there was 99% binding; after 6 hours, there was 98% binding; and after 24 hours, 90% of the $^{99m}$Tc was still bound. After 24 hours, a bioassay in mice was performed on the reconstituted compound. The results indicated that the stannous oxalate-sodium phytate colloid can be used at least up to 24 hours after reconstitution or tagging with $^{99m}$Tc.

The results are summarized in Table VIII below:

TABLE VIII

24 Hour Stability Test on Stannous
Oxalate-Sodium Phytate

| Organ | Bioassay in Mice* % of Injected Activity |
|---|---|
| Liver | 92.3 |
| Spleen | 4.0 |
| Lungs | 0.0 |
| Intestines | 0.9 |
| Kidneys | 0.0 |
| Heart | 0.0 |
| Carcass | 2.9 |

*Average of two mice, uptake time 30 minutes.

EXAMPLE VII

A large production batch of stannous oxalate-sodium phytate colloid was prepared by the following procedure. 373 mg stannous oxalate were weighed into a 5 cc vial containing a small, magnetic stirring bar. 3.0 cc of concentrated HCl was added and the solution was stirred until the stannous oxalate had dissolved. 2.0 ml of this solution were pipetted into a 1 liter flask containing 2.4g. sodium phytate dissolved in 500 ml of water which had been purged with nitrogen gas. The pH of the solution was adjusted to 6.0 with 1N NaOH (about 15 ml). The solution was diluted to 600 ml with nitrogen purged water and stirred until it became clear. The clear solution was filtered through an 0.22 $\mu$ MILLIPORE filter and dispensed as 1 cc aliquots into 10 cc serum vials. The vials were placed in a freezer for freezing, and then lyophilized. A bioassay in mice was performed using an uptake time of 30 minutes and the results were satisfactory with chromatographic analyses showing 94% $^{99m}$Tc binding. The results are summarized in Table IX below:

TABLE IX

Large Production Batch of Stannous
Oxalate-Sodium Phytate Colloid

| Organ | Bioassay in Mice % of Recovered Activity |
|---|---|
| Liver | 90.5 |
| Spleen | 3.6 |
| Intestines | 1.3 |
| Kidneys | 0.5 |
| Heart | <0.1 |
| Lung | 0.1 |
| Carcass | 4.0 |

EXAMPLE VIII

Using the procedure described in Example VII, a batch of stannous oxalate-sodium phytate colloid was prepared for comparison with a non-radioactive reagent useful in liver scanning and commercially available from New England Nuclear, Radiopharmaceutical Division, Atomlight Place, North Bellerica, Massachusetts 01862, stannous phytate containing 20 mg of sodium phytate and 2 mg stannous chloride per vial. Each product was reconstituted with 4 ml of low concentration $^{99m}$Tc (10 mCi/ml). Chromatographic analysis and bioassay tests after an uptake time of 30 minutes were performed on the two reagents. Binding of the $^{99m}$Tc was satisfactory for both reagents. However, the bioassay results show greater stability and low uptake in the lungs and kidney after injection for the technetium-99m labeled liver scanning agent, $^{99m}$Tc - stannous oxalate-sodium phytate, in relation to the high uptake in the lungs and kidney when the technetium-99m labeled liver scanning agent commercially available from New England Nuclear, stannous phytate, was used. The bioassay indicates that there was less free pertechnetate when stannous ion was chelated with oxalate. The high kidney and lung uptake is undesirable in a liver scanning agent because of interference in the liver scan. The results of these tests are summarized in Table X below:

TABLE X
Comparison Study between Two Radiodiagnostic Products Useful in Liver Scanning
Bioassay in Mice
% of Recovered Activity

| Organ | New England Nuclear (using stannous chloride) | $^{99m}$Tc-Stannous Phytate (using stannous oxalate) |
|---|---|---|
| Liver | 81.7 | 90.5 |
| Spleen | 2.4 | 3.6 |
| Intestines | 2.3 | 1.3 |
| Kidneys | 2.0 | 0.5 |
| Heart | 0.5 | < 0.1 |
| Lungs | 3.7 | < 0.1 |
| Carcass | 7.5 | 4.0 |
| % Binding | > 99 | 94.2 |

EXAMPLE IX

Using the procedure described hereinabove in Example VII for preparing a stannous oxalate-sodium phytate colloid, the product colloid was reconstituted with 3 ml of low concentration $^{99m}$Tc (30 mCi of $^{99m}$Tc) and autoclaved for one hour. Better results were obtained by reconstituting with 0.5 cc of saline and then autoclaving for one hour. The autoclaved product was then tagged with 3 ml of low concentration $^{99m}$Tc. It was found that a smaller volume during autoclaving produces a smaller colloid. Hence, it is preferable to tag the colloid after autoclaving it. Moreover, potential contamination and radiation problems associated with autoclaving a radioactive solution are obviated. A comparison of the bioassay in mice after 1 hour uptake is summarized in Table XI below:

TABLE XI
Comparison of Stannous Oxalate-Sodium Phytate Autoclaved by Two Procedures
Bioassay in Mice
% of Total Activity

| Organ | Reconstituted with 3 ml. $^{99m}$Tc-Autoclaved 1 Hour | Reconstituted with 0.5 ml. Saline-Autoclaved 1 Hour |
|---|---|---|
| Liver | 79.5 | 54.4 |
| Spleen | 2.5 | 1.4 |
| Body | 15.7 | 37.4 |
| Intestines | 1.2 | 3.7 |
| Kidneys | 0.5 | 1.5 |
| Heart | < 0.1 | 0.2 |
| Lungs | 0.5 | 1.4 |
| $^{99m}$Tc Binding | ≈ 99% | ≈ 99% |

EXAMPLE X

Using the procedure described hereinabove in Example VII for preparing a stannous oxalate-sodium phytate colloid, a number of batches were prepared. In one batch the colloid was reconstituted with 0.5 ml saline and autoclaved for one hour. Three ml of low concentration $^{99m}$Tc was added to the vial and 1.0 ml was injected into a rabbit. After one hour uptake time, the rabbit was sacrificed and the femur was dissected. The bone marrow was separated by freezing the bone in liquid nitrogen and tapping it out after removing the two ends of the femur. The radioactivity of the bone and bone marrow was then measured and compared on a weight basis. A bone marrow-to-bone ratio of 7 to 1 was obtained. In a similar repetition of the above procedure with a second batch, a 12 to 1 ratio of bone marrow-to-bone was obtained.

In a third batch, the colloid was reconstituted with 0.5 ml. saline and autoclaved for one hour. After 72 hours, 3.0 ml of low concentration $^{99m}$Tc was added to the autoclaved colloid. A bioassay in mice was performed. The product showed excellent stability after autoclaving. The results of the bioassay in mice are summarized in Table XII below:

TABLE XII
Stability of Stannous Oxalate-Sodium Phytate After Autoclaving

| Organ | Bioassay in Mice % of Total Activity* |
|---|---|
| Liver | 60.0 |
| Spleen | 1.6 |
| Body | 32.0 |
| Intestines | 3.7 |
| Kidneys | 1.7 |
| Heart | 0.1 |
| Lungs | 1.0 |

*Average of two mice, uptake time 1 hour

Chromatographic Analysis ~ 99% bound

In a fourth batch, the colloid was reconstituted with 0.5 ml. of saline and autoclaved for different time periods. After one, 4.5 and 9 hours autoclaving, the results of a bioassay in mice after 1 hour uptake are shown in Table XIII below:

TABLE XIII
Effect of Autoclaving Time in Stannous Oxalate-Sodium Phytate
Bioassay in Mice
% of Total Activity
Autoclaving Time

| Organ | 1 Hour | 4.5 Hours | 9 Hours |
|---|---|---|---|
| Liver | 54.5 | 38.5 | 53.3 |
| Spleen | 1.4 | 0.9 | 1.3 |
| Body | 37.4 | 49.0 | 35.3 |

TABLE XIII-continued
Effect of Autoclaving Time in Stannous Oxalate-Sodium Phytate

| | Bioassay in Mice % of Total Activity Autoclaving Time | | |
|---|---|---|---|
| Organ | 1 Hour | 4.5 Hours | 9 Hours |
| Intestines | 3.7 | 5.7 | 6.1 |
| Kidneys | 1.5 | 3.6 | 2.2 |
| Heart | 0.2 | 0.2 | 0.3 |
| Lungs | 1.4 | 2.4 | 1.6 |
| Chromatographic Analysis $^{99m}$Tc Binding | ≈ 99% | ≈ 99% | ≈ 99% |

EXAMPLE XI

A number of samples of stannous oxalate-sodium phytate colloid were prepared according to the method described previously in Example VII. The colloid was reconstituted with 0.5 cc of saline and then autoclaved at 15 psi and 250° F for one hour. Microscopic examination of the colloid showed no particles greater than about 5 microns. Moreover, the colloid was found to be non-toxic and pyrogen-free. Also, stannous analysis of the autoclaved colloid showed that the stannous concentration in the autoclaved samples were the same as non-autoclaved colloid samples. No oxidation occurred during autoclaving.

A comparison was made with two products comprising sodium phytate and stannous chloride which products are commercially available from New England Nuclear, Radiopharmaceutical Division, Atomlight Place, North Bellerica, Massachusetts 01862 and Diagnostic Isotopes, Inc., 123 Pleasant Avenue, Upper Saddle River, New Jersey 07458. The two products were reconstituted with 0.5 cc of saline and autoclaved for one hour to compare them with the stannous phytate colloid of this invention which employs stannous oxalate. A sample from the batch prepared of autoclaved stannous phytate colloid using stannous oxalate as described hereinabove was used for comparison purposes.

The two products containing stannous chloride broke down during autoclaving and were a yellow color. There were no $^{99m}$Tc binding and a bioassay in mice after 1 hour uptake time showed high intestinal uptake which indicates free pertechnetate. A second test was made on the product commercially available from Diagnostic Isotopes, Inc., in which an equivalent amount of sodium oxalate was added to the vial before autoclaving. There was no $^{99m}$Tc binding. This indicates that the stannous must be present as the oxalate to perform as the radiodiagnostic reagent of this invention. The results of the comparison with the two commercial products are summarized in Table XIV below:

TABLE XIV
Comparison of Autoclaved Stannous Phytate Employing Stannous Oxalate to Products Employing Stannous Chloride

| | Bioassay in Mice % of Total Activity | | |
|---|---|---|---|
| Organ | Stannous Oxalate | NEN Product | D.I. Product |
| Liver | 54.5 | 12.4 | 9.6 |
| Spleen | 1.4 | 0.5 | 0.4 |
| Body | 37.4 | 41.5 | 34.9 |
| Intestines | 3.7 | 43.0 | 51.6 |
| Kidneys | 1.5 | 1.6 | 2.1 |
| Heart | 0.2 | 0.3 | 0.3 |
| Lungs | 1.4 | 0.8 | 1.0 |
| Chromatographic Analysis % $^{99m}$Tc Binding | ≈ 99% | 0% | 0% |

EXAMPLE XII

An autoclaved stannous phytate sample was prepared as described in Example XI and tagged with $^{99m}$Tc. A 24 hour blood clearance study was performed on mice using the autoclaved sample. Each mouse was injected with 0.2 cc containing 1.70 mCi of $^{99m}$Tc activity. The results are similar to that obtained with non-autoclaved stannous oxalate-sodium phytate colloid in Example V previously. The results are summarized in Table XV below:

TABLE XV
Blood Clearance of Autoclaved $^{99m}$Tc-Stannous Oxalate-Sodium Phytate in Mice

| Uptake Time | % of Injected Activity in Blood |
|---|---|
| 30 min. | 3.0 |
| 1 hr. | 1.7 |
| 2 hrs. | 2.0 |
| 3 hrs. | 1.3 |
| 4 hrs. | 1.8 |
| 6 hrs. | 1.6 |
| 24 hrs. | 0.6 |

In addition, the organ distribution vs. time was determined with the autoclaved sample. Each mouse was injected with 0.2cc of the autoclaved product and, after various time intervals, the mice were sacrificed and a bioassay performed. After 24 hours, the colloid is still in the liver, which is similar to a $^{99m}$Tc-sulfur colloid. The results are summarized in Table XVI hereinbelow:

TABLE XVI
Organ Distribution of Autoclaved Stannous Oxalate-Sodium Phytate Colloid in Mice

| | Bioassay in Mice* % of Activity | | | | | | |
|---|---|---|---|---|---|---|---|
| Uptake Time | Liver | Spleen | Lung | Kidney | Heart | Intestines | Carcass |
| 30 min. | 53.8 | 1.3 | 1.4 | 3.1 | 0.2 | 3.3 | 37.0 |
| 1 hr. | 61.7 | 1.4 | 0.7 | 2.1 | 0.0 | 3.5 | 30.8 |
| 2 hrs. | 65.1 | 1.3 | 0.6 | 2.4 | 0.0 | 3.9 | 26.9 |
| 3 hrs. | 63.0 | 1.3 | 0.6 | 1.9 | 0.0 | 3.6 | 30.0 |
| 4 hrs. | 62.1 | 1.7 | 0.5 | 1.8 | 0.1 | 3.8 | 30.1 |
| 6 hrs. | 60.3 | 0.9 | 0.6 | 2.1 | 0.1 | 3.3 | 32.7 |
| 24 hrs. | 73.5 | 1.3 | 0.8 | 1.3 | 0.1 | 2.3 | 21.0 |

*Average of two mice

The urine clearance in mice of another autoclaved stannous oxalate-sodium phytate colloid sample was determined. Five mice were injected and tested over a 24-hour period. The results show that urine clearance is much more rapid when the autoclaved stannous oxalate-sodium phytate colloid is used than when an unautoclaved product is used. The results are summarized in Table XVII below:

TABLE XVII
Urine Clearance of Autoclaved Stannous Oxalate-Sodium Phytate

| Time After Injection | % of Injected Activity Excreted |
|---|---|
| 30 min. | 8.9 |

TABLE XVII-continued
Urine Clearance of Autoclaved Stannous Oxalate-Sodium Phytate

| Time After Injection | % of Injected Activity Excreted |
|---|---|
| 1 hr. | 20.4 |
| 2 hrs. | 27.3 |
| 3 hrs. | 30.0 |
| 4 hrs. | 31.8 |
| 24 hrs. | 42.5 |

Still another sample of the stannous oxalate-sodium phytate colloid prepared as described previously was autoclaved with 0.5 ml of saline. 6 ml of high concentration $^{99m}$Tc (30 mCi/ml) was added to the autoclaved product. A bioassay in mice shows results comparable to those shown in Examples XI and XII and the $^{99m}$Tc binding was about 99%. This shows that high activity $^{99m}$Tc and 6 ml of added volume works satisfactorily with the bone marrow radiodiagnostic agent of this invention.

EXAMPLE XIII

Two samples of stannous oxalate-sodium phytate prepared as described in Example VII were reconstituted with 0.5 ml of saline and autoclaved for one hour. To one sample, 6 ml of high concentration pertechnetate was added and to the other sample, 3 ml of low concentration pertechnetate was added. After standing for 24 hours and 1 hour, respectively, a bioassay on mice was performed in both cases. After 24 hours, the % $^{99m}$Tc binding dropped from greater than 99% to 91%. This is also indicated in the bioassay which shows a greater intestinal uptake of activity over 24 hours. However, the formulation still provides a satisfactory bone marrow agent. The results are summarized in Table XVIII below:

TABLE XVIII
24 Hour Stability Test on Autoclaved Stannous Oxalate-Sodium Phytate
Bioassay in Mice*
% of Total Activity

| Organ | 3 ml. TcO$_4^-$ 1 Hr. Standing | 6 ml. TcO$_4^-$ 24 Hr. Standing |
|---|---|---|
| Liver | 56.6 | 48.7 |
| Spleen | 1.7 | 2.7 |
| Body | 35.4 | 39.7 |
| Intestines | 3.7 | 5.7 |
| Kidneys | 1.5 | 2.0 |
| Heart | 0.1 | 0 |
| Lungs | 1.2 | 1.3 |
| *Average of two mice, uptake time 1 hour | | |
| % $^{99m}$Tc Binding | > 99% | 91.1% |

EXAMPLE XIV

Several vials of stannous oxalate-sodium phytate colloid prepared as described in Example VII were reconstituted with 0.5 ml saline and autoclaved for one hour. Each day for seven days, one vial was tested by adding 3 ml of low concentration $^{99m}$Tc and performing a bioassay in mice. The % $^{99m}$Tc binding remained greater than 99% in all cases and the reagent would be considered a satisfactory bone marrow agent. A user could autoclave several vials of the stannous oxalate-sodium phytate at the beginning of one week and use a vial daily at least 7 days. The results are summarized in Table XIX below:

TABLE XIX
Seven Day Test on Autoclaved Stannous Oxalate-Sodium Phytate Bone Marrow Agent
Bioassay in Mice*
% of Total Activity
Time After Autoclaving (Days)

| Organ | 1 | 2 | 3 | 6 | 7 |
|---|---|---|---|---|---|
| Liver | 60.9 | 65.4 | 68.5 | 66.8 | 67.2 |
| Spleen | 1.8 | 2.2 | 1.8 | 1.2 | 1.5 |
| Body | 30.3 | 26.2 | 24.4 | 26.1 | 24.8 |
| Intestines | 3.9 | 3.6 | 3.3 | 3.6 | 3.8 |
| Kidneys | 2.2 | 1.8 | 1.6 | 1.4 | 2.2 |
| Heart | 0.1 | 0.2 | 0.0 | 0.1 | 0.0 |
| Lungs | 0.8 | 0.9 | 0.5 | 0.9 | 0.5 |

*Average of two mice, uptake time 1 hour.

EXAMPLE XV

Several vials of stannous oxalate-sodium phytate colloid prepared according to the procedure described in Example VII were reconstituted with 0.5 ml of saline and autoclaved for one hour. To test the effect of volume and total activity, four vials were injected with 1, 2, 4 and 5 ml of low concentration $^{99m}$Tc (10 mCi/ml.). A bioassay on mice was performed. The 1 ml volume showed poor $^{99m}$Tc binding which indicates that the minimum volume of pertechnetate employed should be at least about 2.0 ml. Up to 50 mCi of $^{99m}$Tc activity may be added without effect. The results of the bioassay in mice are summarized in Table XX below:

TABLE XX
Effect of Volume of Pertechnetate on Stannous Oxalate-Sodium Phytate Bone Marrow Agent
Bioassay in Mice*
% of Total Activity
Volume of Low Conc. $^{99m}$Tc Added (ml.)

| Organ | 1 | 2 | 4 | 5 |
|---|---|---|---|---|
| Liver | 71.6 | 70.7 | 68.7 | 65.7 |
| Spleen | 2.2 | 1.5 | 1.6 | 1.9 |
| Body | 22.2 | 23.3 | 23.7 | 25.8 |
| Intestines | 2.6 | 2.6 | 3.6 | 3.8 |
| Kidneys | 0.9 | 1.2 | 1.7 | 1.8 |
| Heart | 0.0 | 0.1 | 0.1 | 0.1 |
| Lungs | 0.5 | 0.5 | 0.7 | 1.0 |
| *Average of two mice, uptake time 1 hour. | | | | |
| % $^{99m}$Tc Binding | 86% | > 99% | > 99% | > 99% |

EXAMPLE XVI

A number of vials of lyophilized stannous oxalate-sodium phytate colloid prepared according to the procedure described in Example VII were reconstituted with 0.5 ml of saline and autoclaved at various autoclave pressures and for various times. The autoclaved products were labeled with $^{99m}$Tc and a bioassay in mice after 1 hour uptake time was performed. As the pressure and temperature of autoclaving was increased, there was a corresponding increase in body uptake. The binding remained greater than 99% in all cases. Average pressures typically used are about 16 psi. An autoclave time of about 2 hours achieved the same effect, i.e., a larger body uptake. A large body, uptake indicates increased bone marrow if there is no free pertechnetate present. The results of the bioassay in mice are summarized in Table XXI below:

TABLE XXI

Effect of Autoclaving Time and Pressure on Stannous Oxalate-Sodium Phytate

Bioassay in Mice
% of Total Activity

| Pressure | Time (Hr.) | Liver & Spleen | Kidney & Intestines | Body (Organs Removed) |
|---|---|---|---|---|
| 15 (250° F) | 1 | 76.3 | 4.4 | 18.3 |
| 15 | 1 | 74.4 | 4.2 | 20.8 |
| 20(259° F) | 1 | 60.4 | 4.8 | 33.9 |
| 22 (262° F) | 1 | 61.6 | 6.6 | 30.7 |
| 24 (256° F) | 1 | 64.6 | 4.7 | 30.0 |
| 16 (252° F) | 2 | 54.5 | 7.4 | 36.0 |
| 16 | 2 | 59.2 | 6.3 | 33.4 |

EXAMPLE XVII

Several vials of lyophilized stannous-oxalate-sodium phytate colloid prepared according to the procedure described in Example VII were reconstituted with 0.5 ml of saline and autoclaved for two hours at 15 psi pressure. A bioassay test in mice was performed. The results show that the autoclaved colloid could be used for at least 8 days. The results are summarized in Table XXII below:

TABLE XXII

**8-Day Test on Autoclaved* Stannous Oxalate-Sodium Phytate Bone Marrow Agent**

Bioassay in Mice**
% of Total Activity
Time after Autoclaving (Days)

| Organ | 1 | 4 | 5 | 6 | 7 | 8 |
|---|---|---|---|---|---|---|
| Liver | 66.8 | 55.4 | 61.8 | 64.9 | 59.7 | 54.3 |
| Spleen | 1.4 | 1.6 | 1.4 | 1.8 | 1.9 | 1.8 |
| Body | 26.7 | 32.8 | 29.6 | 27.4 | 30.8 | 34.4 |
| Intestines | 3.3 | 6.6 | 4.0 | 3.5 | 4.2 | 5.4 |
| Kidneys | 1.2 | 2.6 | 2.0 | 1.8 | 2.6 | 3.0 |
| Heart | 0.1 | 0.2 | 0.1 | 0.1 | 0.1 | 0.2 |
| Lungs | 0.5 | 0.7 | 1.0 | 0.6 | 0.7 | 0.8 |

*Autoclaved at 15 psi for 2 hours
**Average of two mice, uptake time 1 hour
Chromatographic Analysis - greater than 99% binding

EXAMPLE XVIII

Several vials of lyophilized stannous oxalate-sodium phytate reagent prepared according to the procedure described in Example VII were reconstituted with 0.5 ml of saline and autoclaved for 2 hours at 15 psi. The autoclaved samples were then lyophilized again. The samples were tested by adding pertechnetate and performing a bioassay in mice after 1 hour uptake time. The results indicate the autoclaved and relyophilized samples would still be a satisfactory bone marrow agent and are summarized in Table XXIII below:

TABLE XXIII

Test on Freeze Dried-Autoclaved Stannous Oxalate-Sodium Phytate

| Organ | Bioassay in Mice % of Total Activity |
|---|---|
| Liver | 66.8 |
| Spleen | 1.6 |
| Body | 24.4 |
| Intestines | 4.4 |
| Kidneys | 2.0 |
| Heart | 0.2 |
| Lungs | 0.7 |
| Chromatographic Analysis | > 99% bound |

EXAMPLE XIX

A batch of stannous oxalate-sodium phytate was prepared according to the procedure described in Example VII. The bulk solution of 250 ml was then autoclaved for 2 hours in a sealed vial under nitrogen. This solution was then dispensed into serum vials and freeze dried. The product was then reconstituted with 3.0 ml of $^{99m}$Tc and evaluated by a bioassay in mice after 1 hour uptake time and by chromatography. The results show that it does work as a satisfactory bone marrow agent and are summarized in Table XXIV below:

TABLE XXIV

Tests on Stannous Oxalate-Sodium Phytate Autoclaved in Bulk

| Organ | % of Total Activity |
|---|---|
| Liver | 73.8 |
| Spleen | 2.0 |
| Body | 19.4 |
| Intestines | 2.4 |
| Kidneys | 1.2 |
| Heart | 0.1 |
| Lungs | 1.0 |
| Chromatographic Analysis | > 99% bound |

EXAMPLE XX

Vials of lyophilized stannous oxalate-sodium phytate prepared according to the procedure described in Example VII were stored for 224 days at 40° C and 225 days at 70° C, respectively. Samples of these stored vials were evaluated both chromatographically and by bioassay in mice after 30 minutes uptake time. The samples stored at 70° C increased in body uptake and the $^{99m}$Tc binding was still greater than 99%. The results are summarized in Table XXV below:

TABLE XXV

Accelerated Shelf-Life Studies on Stannous Oxalate-Sodium Phytate

Bioassay in Mice
% of Total Activity

| Organ | Stored at 40° C for 224 Days | Stored at 70° C for 225 Days |
|---|---|---|
| Liver | 89.2 | 68.6 |
| Spleen | 3.9 | 1.6 |
| Body | 5.0 | 26.2 |
| Intestines | 1.2 | 2.2 |
| Kidneys | 0.5 | 1.2 |
| Heart | 0 | 0 |
| Lungs | 0 | 0.2 |
| Chromatographic Analysis | > 99% | > 99% |

EXAMPLE XXI

Samples of stannous oxalate-sodium phytate prepared according to the procedure described in Example VII were reconstituted with 0.5 cc of saline and then autoclaved for 2 hours at 15 psi. Samples were then evaluated chromatographically and by a bioassay on mice (uptake time 1 hour) after the addition of 3.0 cc of $^{99m}$Tc. Several autoclaved vials were retained for evaluation 84 days later. After 84 days storage, the results for the pre-autoclaved stannous oxalate-sodium phytate were satisfactory when compared to the results for the stannous phytate reagent when tested after 4 days. The results are summarized in Table XXVI below:

TABLE XXVI

Shelf-Life Test on Pre-Autoclaved Phytate

Bioassay on Mice
% of Total Activity

| Organ | 4 Days' Storage | 84 Days' Storage |
|---|---|---|
| Liver | 55.4 | 54.4 |
| Spleen | 1.6 | 2.0 |
| Intestines | 6.6 | 5.4 |
| Kidneys | 2.6 | 3.4 |

TABLE XXVI-continued
Shelf-Life Test on Pre-Autoclaved Phytate

Bioassay on Mice
% of Total Activity

| Organ | 4 Days' Storage | 84 Days' Storage |
|---|---|---|
| Heart | 0.2 | 0.1 |
| Lungs | 0.7 | 1.5 |
| Carcass | 32.8 | 33.2 |

EXAMPLE XXII

Samples of stannous oxalate-sodium phytate were prepared according to the procedure described in Example VII, except that the sodium phytate concentration was varied between 0.1 mg and 20 mg/ml before lyophilizing. Samples of the final preparation were tested with and without autoclaving. The percent bone marrow uptake in mice is determined by observing the body uptake. If there is no unbound $^{99m}$Tc, then it is assumed that the activity is in the bone or bone marrow. The results (1 hour uptake time) of the tests performed indicate that there was no improvement in the body uptake over the range tested. The results are summarized in Table XXVII below:

TABLE XXVII
Effect of Sodium Phytate Concentration on Bone Marrow Uptake

| Sodium Phytate Conc. (mg/ml) | % Body Uptake | |
|---|---|---|
| | Not Autoclaved | Autoclaved |
| 0.1 | 4.6 | 11.6 |
| 1.0 | 8.0 | 26.8 |
| 8 | 2.5 | 15.8 |
| 20 | 4.6 | 15.0 |

Those skilled in the art will appreciate that the particular examples of this invention described hereinabove are intended to be illustrative only and are not intended to limit the scope of the invention.

What is claimed is:

1. A stable, non-radioactive carrier suitable for liver scanning when labeled with $^{99m}$Tc, said carrier comprising sodium phytate; and stannous ion chelated with oxalate, the ratio by weight of said phytate to chelate being at least about 1 to 1.

2. A carrier as defined in claim 1 wherein said ratio is at least about 3 to 1.

3. A carrier as defined in claim 2 wherein said ratio is at least about 13 to 1.

4. A carrier as defined in claim 2 wherein said ratio is between about 3 to 1 and about 20 to 1 and said pH is about 6.

5. A stable, non-radioactive carrier solution having a pH between about 3 and about 7, said solution being suitable for bone marrow scanning when autoclaved and labeled with $^{99m}$Tc, said solution comprising sodium phytate; stannous ion chelated with oxalate, and an aqueous solution, the ratio by weight of said phytate to said chelate being at least about 1 to 1.

6. A method of preparing a stable, radioactive carrier suitable for liver scanning when labeled with $^{99m}$Tc and suitable for bone marrow scanning when autoclaved and then labeled with $^{99m}$Tc, said method comprising; dissolving sodium phytate in an aqueous solution free of entrained oxygen to form a first solution; dissolving stannous oxalate in a non-oxidizing acid to form a second solution, the ratio by weight of said first amount to said second amount being at least about 1 to 1;
contracting said first solution with said second solution to form a third solution; and
adjusting the pH of said third solution to between about 4 and about 7.

7. A method as defined in claim 6 wherein said non-oxidizing acid is selected from the group consisting of hydrochloric, acetic, sulfuric and phosphoric acid and said ratio is at least about 3 to 1.

8. A method as defined in claim 7 wherein said ratio is at least about 13 to 1.

9. A method as defined in claim 7 wherein said ratio is between about 3 to 1 and about 20 to 1, said pH is about 6 and said non-oxidizing acid is hydrochloric acid.

10. A method as defined in claim 6 further including: adjusting the concentration of said third solution to a predetermined concentration.

11. A method as defined in claim 10 further including: lyophilizing said third solution at a temperature below about 30° C to form a solid.

12. A method as defined in claim 11 wherein when said third solution is lyophilized at a temperature between about 30° C and about −10° C.

13. A method as defined in claim 12 further including: redissolving said lyophilized solid in an aqueous solution.

14. A method as defined in claim 6 further including: autoclaving said third solution at a temperature of from about 240° F to about 290° F, for a time period between about 1 hour and about 6 hours and at a pressure between about 10 to about 43 psi to form a colloid.

15. A method as defined in claim 14 wherein said autoclave temperature is about 270° F, said autoclave time period is about 2 hours and said autoclave pressure is about 28 psi.

16. A method as defined in claim 13 further including: autoclaving said redissolved solution at a temperature of from about 240° F to about 290° F, for a time period between about 1 hour and about 6 hours and at a pressure between about 10 to about 43 psi to form a colloid.

17. A method as defined in claim 16 wherein said autoclave temperature is about 270° F, said autoclave time period is about 2 hours and said autoclave pressure is about 28 psi.

18. A method as defined in claim 6 wherein said third solution is contacted with a sufficient amount of a saline solution of Na$^{99m}$TcO$_4$ to form a 99mTc-labeled radiodiagnostic agent suitable for liver scanning.

19. A method as defined in claim 13 wherein said redissolved solution is contacted with a sufficient amount of a saline solution of Na$^{99m}$TcO$_4$ to form a $^{99m}$Tc-labeled radiodiagnostic agent suitable for liver scanning.

20. A method as defined in claim 14 wherein said autoclaved colloid is contacted with a sufficient amount of a saline solution of Na$^{99m}$TcO$_4$ to form a $^{99m}$Tc-labeled radiodiagnostic agent suitable for bone marrow scanning.

21. A method as defined in claim 16 wherein said autoclaved colloid is contacted with a sufficient amount of a saline solution of Na$^{99m}$TcO$_4$ to form a $^{99m}$Tc-labeled radiodiagnostic agent suitable for bone marrow scanning.

22. A radiodiagnostic agent suitable for liver scanning and having a pH between about 3 and about 7, said agent comprising sodium phytate; stannous ion chelated with oxalate, and a saline solution of Na$^{99m}$TcO$_4$, the ratio by weight of said phytate to said chelate being at least about 1 to 1.

23. A stable, non-radioactive colloid suitable for bone marrow scanning when labeled with $^{99m}$Tc, said colloid comprising an autoclaved mixture of sodium phytate; stannous ion chelated with oxalate, and an aqueous solution, the ratio by weight of said phytate to said chelate being at least about 1 to 1, said colloid having a particle size less than about 1 micron.

24. A radiodiagnostic colloid suitable for bone marrow scanning and having a pH between about 3 and about 7, said colloid comprising sodium phytate; stannous ion chelated with oxalate, and a saline solution of Na$^{99m}$TcO$_4$, the ratio by weight of said phytate to said chelate being at least about 1 to 1, said colloid having a particle size less than about 1 micron.

* * * * *